: US008684911B2

(12) United States Patent
Gorini et al.

(10) Patent No.: US 8,684,911 B2
(45) Date of Patent: Apr. 1, 2014

(54) SELF-PROPELLED ENDOSCOPIC DEVICE

(75) Inventors: Samuele Gorini, Pisa (IT); Alberto Arena, Cascina (IT); Giuseppe Pernorio, Pisa (IT); Arianna Menciassi, Pisa (IT); Paolo Dario, Leghorn (IT)

(73) Assignee: ERA Endoscopy S.R.L., Peccioli (IT)

( * ) Notice: Subject to any disclaimer, the term of this patent is extended or adjusted under 35 U.S.C. 154(b) by 1565 days.

(21) Appl. No.: 11/607,754

(22) Filed: Nov. 30, 2006

(65) Prior Publication Data
US 2007/0179339 A1    Aug. 2, 2007

(30) Foreign Application Priority Data

Nov. 30, 2005 (EP) .................................. 05425854

(51) Int. Cl.
*A61B 1/00* (2006.01)

(52) U.S. Cl.
USPC ........ 600/114; 600/115; 600/156; 604/95.01; 604/95.02

(58) Field of Classification Search
USPC ......... 600/101, 141, 106, 114–116, 138, 139, 600/104; 604/95.01–95.05
See application file for complete search history.

(56) References Cited

U.S. PATENT DOCUMENTS

| | | | |
|---|---|---|---|
| 5,398,670 A | 3/1995 | Ortiz et al. ......................... 128/6 |
| 5,662,587 A * | 9/1997 | Grundfest et al. ............. 600/114 |
| 5,906,591 A | 5/1999 | Dario et al. ..................... 604/95 |
| 2002/0158392 A1 * | 10/2002 | Petrina ........................... 267/168 |
| 2004/0073082 A1 * | 4/2004 | Phee Soo Jay et al. ........ 600/101 |
| 2005/0070949 A1 | 3/2005 | Bakos et al. |

FOREIGN PATENT DOCUMENTS

| | | | |
|---|---|---|---|
| WO | 02068035 | 9/2002 | ............ A61M 25/01 |
| WO | 03053505 | 7/2003 | ............ A61M 25/01 |
| WO | 2005094665 | 10/2005 | ............... A61B 1/00 |

OTHER PUBLICATIONS

European Search Report, dated May 10, 2006, for European Patent Application No. EP 05 42 5854.
European Communication mailed on Jan. 31, 2012 for Application No. 05425854.6 filed on Nov. 30, 2005.
European Communication mailed on Nov. 6, 2012 for Application No. 05425854.6 filed on Nov. 30, 2005.

* cited by examiner

*Primary Examiner* — Matthew J Kasztejna
*Assistant Examiner* — Ryan Henderson
(74) *Attorney, Agent, or Firm* — Steinfl & Bruno, LLP

(57) ABSTRACT

An endoscopic device for autonomous locomotion through a selected body cavity in a predetermined direction, the device comprising a hollowed, cylindrical body that extends between two, preferably, the front and rear, end portions, respectively. The body is made of a relatively elastic material and includes an anchor for temporarily and alternately attaching the end portions to a wall portion of the body cavity in synch with corresponding axial extensions and contractions of the body. The body incorporates a reinforcement structure distributed along its length that is substantially rigid in a radial direction and yields in an axial direction, the structure specifically comprising either a plurality of relatively rigid rings or at least one helical spring.

7 Claims, 2 Drawing Sheets

SELF-PROPELLED ENDOSCOPIC DEVICE

FIELD OF THE INVENTION

The present invention relates generally to medical devices and, more particularly, to a device suitable for locomotion through a body cavity.

BACKGROUND OF THE INVENTION

Endoscopic devices are typically used by surgeons for a variety of surgical and/or diagnostic procedures. In operation, a surgeon manually applies a force, for instance, directly to the device in order to impart forward motion through a patient's body. Such devices are usually operated in conjunction with other surgical and/or diagnostic instruments, e.g., micro-arms, micro-cameras and/or laser emitters, that may be needed to complete various medical procedures.

Endoscopic devices often associated and/or used in conjunction with surgical and/or diagnostic instruments, as may be needed to complete various procedures include, e.g., micro-arms, micro-cameras and/or laser emitters. Accordingly, the instruments associated with endoscopic devices are operated by the surgeon concurrently, the surgeon applying a force to the device in order to impart their forward motion through the patient's body as well.

Other conventional endoscopic devices, however, are not capable of autonomous or semi-autonomous locomotion through a patient's body cavity of a patient. These devices comprise a tubular body of variable length with two, front and rear end portions, and an anchor for providing temporary and alternate attachment of the front end portion or rear end portions to a wall of the body cavity, thereby enabling forward motion of the device.

The variable-length tubular body of the device is a bellows-shaped tube capable of being extended or contracted through air injected therein or aspirated therefrom. In one arrangement, the device is anchored to the wall of the body cavity by a clamp associated with the front and rear end portions of the device and selectively enabled by an external control unit in synch with the successive extensions and contractions of the bellows-shaped tubular body. The clamp is actuated pneumatically by bellows-shaped members.

Once the bellows-shaped tubular body has been extended, a positive pressure is created inside the body using compressed air, thereby achieving elongation in proportion to the pressure inside, while the body contracts through progressive reduction of the pressure inside the body, until some degree of vacuum is created.

Although it has the considerable flexibility needed to negotiate the narrow intestinal loops without causing pain, the device according to the above-mentioned PCT patent application has several functional drawbacks due to its relative extendibility and friction between its outer surface and the walls of the body cavity, which have a negative effect on the device's efficiency of locomotion. Because the intestinal walls adhere partially or totally to the outer surface of the bellows, the intestinal tissue may be trapped between the folds of the bellows du ring the contraction stage. Though it does no damage the mucosa, this interferes with the progress of the device through the intestines. Moreover, given the elasticity of the mesentery and intestinal tissues, any friction between the surface of the tubular bellows-shaped body and the walls of the body cavity will stretch the tissue and mesentery instead of making the device slide along the walls, thus preventing any forward motion of the device relative to the intestinal walls during the extension stage, then allowing the tissues of the tubular cavity and the mesentery to return to their original position (with a so-called "accordion effect") during the contraction stage.

It should be noted, moreover, that the considerable thickness of the bellows-shaped tubular body (in terms of the difference between the maximum radius and the minimum radius of the contracted and extended bellows) results in a significant reduction in the space actually available inside it, making difficult the passage of the compressed air tubes needed for the displacement of the device and making it necessary to use smaller-diameter tubes, with a consequent increase in the pressure drop and reduction in the device's speed of locomotion.

OBJECTS AND SUMMARY OF THE INVENTION

Accordingly, it is an object of the present invention to provide a self-propelled endoscopic device that provides the same degree of flexibility as conventional autonomous or semi-autonomous endoscopic devices, but without hindering the efficiency of its locomotion during use.

Another object of the present invention is to provide a self-propelled endoscopic device with a tubular body having both considerable capacity for extension and a low coefficient of friction to avoid any entrainment of the tissues forming the wall of the body cavity and, thereby, ensure effective locomotion of the device.

A further object of the present invention is to provide a self-propelled endoscopic device with a significantly more spacious interior, while maintaining the same outer diameter, than is available in conventional endoscopic devices with bellows-shaped bodies, thereby enabling the body interior to be used more efficiently, such as for allowing the passage of service tubes.

Still another object of the present invention is to provide a self-propelled endoscopic device, wherein its tubular body, or the actuators of the anchor on its front and rear end portions, contract without circumferential surface folds in which tissues of the wall forming the body cavity, through which the endoscopic device advances may become trapped.

These objects are achieved by the improved endoscopic device according to the present invention, in which its tubular body is made of an elastic material and incorporates a reinforcement structure distributed along its length that is substantially rigid in the radial direction and yielding in the axial direction. In the preferred embodiments, said reinforcement consists either of a plurality of substantially rigid rings, or of at least one coaxial spring, or preferably a pair of springs wound crosswise to one another, incorporated within its thickness.

BRIEF DESCRIPTION OF THE DRAWINGS

A specific, illustrative self-propelled endoscopic device, according to the present invention, is described below with reference to the accompanying drawings, in which.

The same numerals are used throughout the drawing figures to designate similar elements. Still other objects and advantages of the present invention will become apparent from the following description of the preferred embodiments.

DETAILED DESCRIPTION OF THE PREFERRED EMBODIMENTS

Figure 1:
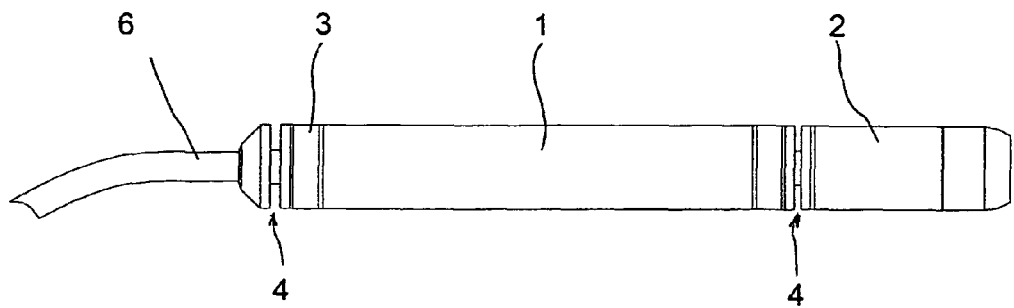
FIG. 1 shows schematically a self-propelled endoscopic device, according to one aspect of the present invention.

Referring now to the drawings and, more particularly, to FIGS. 1-6, there is shown generally a self-propelled endoscopic device, in accordance with various aspects of the present invention. According to one embodiment, as set forth in FIG. 1, the device comprises a tubular body 1 extending between two end portions, referred to generally as front and rear end portions 2 and 3, respectively, the terms front and rear referring to the device's direction of locomotion through a selected body cavity, as indicated generally by arrow F. In this manner, the device is preferably and advantageously moveable in both forward and reverse directions within the body cavity.

Respective front and rear end portions 2, 3 include an anchor 4, e.g., a clamp, by which the device temporarily and alternately becomes attached to the wall of the body cavity to enable device locomotion in a conventional manner.

Figure 2:
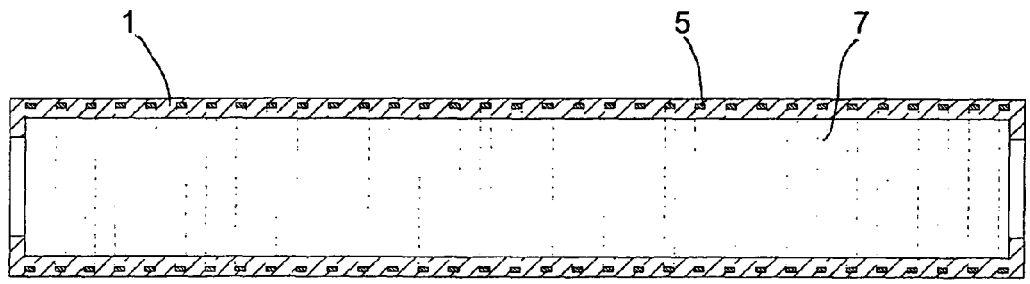
FIG. 2 is an enlarged sectional view of a central tubular body of an endoscopic device, according to another aspect of the present invention.

According to the present invention, tubular body 1 is made of a low-hardness elastomeric material, e.g., Shore A 10 silicone. The tubular body has a structural reinforcement comprising, in one embodiment of the present invention, as illustrated in FIG. 2, a plurality of rings 5 made of a rigid material, e.g., Shore A 80 silicone, such reinforcement defining a hollow cylindrical portion 7 of tubular body 1.

The rear end portion 3 is connected to an external control unit by a hose 6, which houses services tubes, including, but not limited to, tubing necessary for delivering compressed air inside tubular body 1, or for creating a negative pressure therein, thereby inducing extension or retraction of the tubular body that is necessary for so-called inchworm type locomotion.

Figure 3:
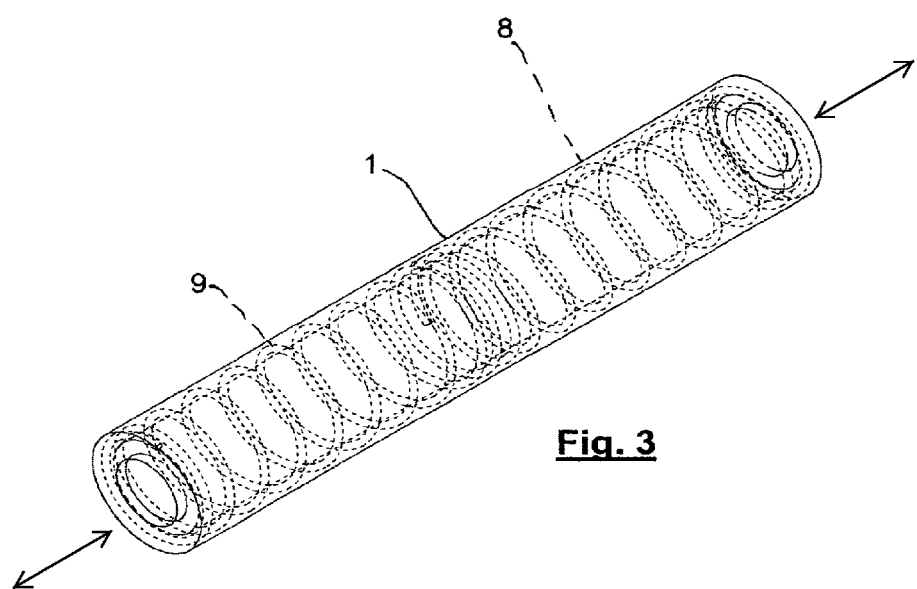
FIG. 3 is a perspective view of a central tubular body of an endoscopic device, according to a further aspect of the present invention.
Figure 4:
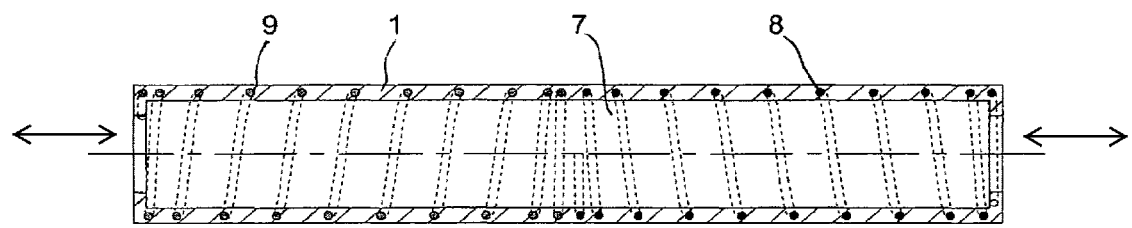
FIG. 4 is a sectional view taken longitudinally of the central tubular body shown in FIG. 3.

In an alternative embodiment of the invention, illustrated in FIGS. 3 and 4, 1 is reinforced with a pair of made of a rigid material, e.g. one another the silicone tubular body helical springs 8 and 9 steel, wound crosswise to one another.

In both cases, the presence of the plurality of rings or of the two coaxial springs prevents any radial dilation or collapse of the tubular body 1, while still allowing its extension and retraction in the axial direction according to changes in the internal pressure conditions. Extension and contraction of the body is indicated by the arrows at the axial position of the device.

In the case involving a pair of helical springs, 8 and 9, the arrangement of the springs with the windings lying crosswise to one another prevents any related rotation of the device's end portions 2 and 3 (which would induce a continuous rotation of the image transmitted by a TV camera installed in the front end portion 2) or any twisting of the hose 6 extending from the rear end portion 3. The fact that the two springs 8 and 9 are wound crosswise to one another also facilitates the sliding of the tissue of the body cavity over the outer surface of the tubular body 1.

Figure 5:
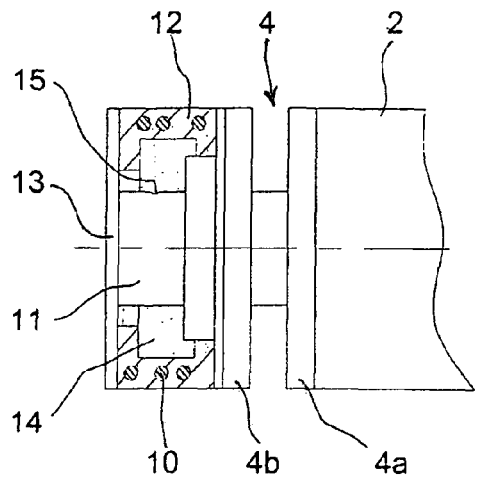
FIG. 5 illustrates schematically an end portion of an endoscopic device, according to one aspect of the present invention, having an anchor in an open position.
Figure 6:
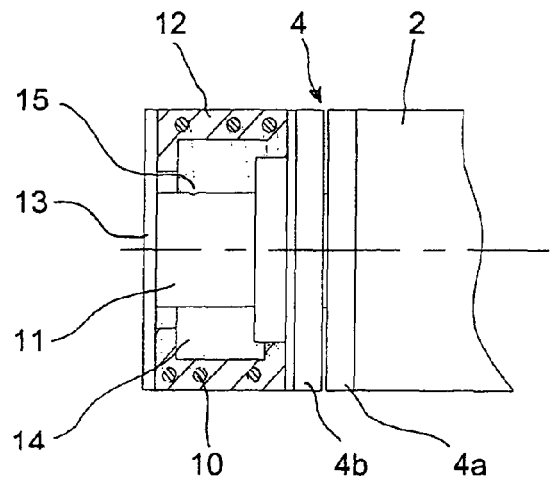
FIG. 6 is a schematic illustration of the device shown in FIG. 5 with the anchor in a closed position.

Silicone tubing reinforced with rings 5, or a helical spring 10, as illustrated in FIGS. 5 and 6, can also be used for the actuating device that controls the opening and closing of the anchoring means 4 installed at the front 2 and rear 3 end portions of the endoscopic device. As illustrated in the above-mentioned figures, the anchoring means 4 comprise a pair of circular jaws 4a and 4b, the former of which is fixed, while the latter is movable with respect to the former. In particular, the movable jaw 4b is slidingly mounted on a tubular member 11 extending at right angles from a connection flange 13 by means of which the end portion 2 is axially connected to the tubular body 1. The movable jaw 4b is also connected to the flange 13 by means of a silicone tube 12 with a helical spring 10 (in the case illustrated) incorporated within its thickness. The tube 12 delimits a chamber 14 into which compressed air can be delivered or a negative pressure can be created through a hole 15 in the tubular member 11. The creation of a positive or negative pressure in the chamber 14 results in the extension or contraction of the tube 12, which in turn makes the movable jaw 4b slide one way or the other and, as a consequence, respectively close or open the anchoring means 4.

The improvement according to the present invention, applied both to the tubular body and to the pneumatic actuators of the anchoring means, ensures an efficient locomotion of the endoscopic device, overcoming all the above-mentioned drawbacks of the known devices. In fact, the outer surface of the device remains smooth and slippery both in extension and in contraction, without any folds formation in which the tissue of the body cavity wall could be trapped. Moreover, the absence of the typical folds of a bellows design leads to an increase in the ratio of the internal to the external diameter of the device, affording a significantly larger internal volume for the same external diameter, which facilitates the passage of the service tubes. Finally, the highly-extendable tubular body 1 combines with a low friction coefficient to prevent any stretching of the body cavity wall tissues, which would slow down the forward displacement of the device reducing its locomotion efficiency.

Various modifications and alterations may be appreciated based on a review of this disclosure. These changes and additions are intended to be within the scope and spirit of the invention as defined by the following claims.

What is claimed is:

1. An endoscopic device for self-propelled locomotion through a selected body cavity in a predetermined direction, comprising a hollowed, cylindrical non-bellows type body constructed of a relatively elastic material extending between two end portions, with anchors suitable for temporarily and alternately attaching the end portions to a selected wall portion of the body cavity in synch with corresponding extensions and contractions axially of the cylindrical body, and pneumatic devices for actuating the anchors, wherein walls of the cylindrical body incorporate a reinforcement structure including at least one spring distributed along an entire length of the cylindrical body, wherein the spring is rigid in a radial direction and yields in an axial direction, so as to provide elongation and contraction of the cylindrical body concurrently through such axial yieldability of the reinforcement structure while preventing radial dilation or collapse of the cylindrical body.

2. The endoscopic device set forth in claim 1, wherein the pneumatic devices comprise a hollowed cylindrical member constructed of a relatively flexible elastic material incorporating the reinforcement structure, joined axially to a moveable member of the anchors and to the hollowed, cylindrical body, and capable of extending and contracting cyclically in response to positive and negative pressures created in an internal chamber of the cylindrical body, and thereby effecting respective closing and opening of the anchors.

3. The endoscopic device set forth in claim 2, wherein the anchors are of a clamp type, and are formed generally of a fixed jaw and a mobile jaw, to which the hollowed, cylindrical member is connected.

4. The endoscopic device set forth in claim 2, wherein the at least one spring is a helical spring incorporated coaxially within a thickness of the cylindrical body and the hollowed, cylindrical member.

5. The endoscopic device set forth in claim 1, wherein the elastic and flexible material is a low-hardness silicone.

6. The endoscopic device set forth in claim 1, wherein an outer surface of the endoscopic device remains smooth and slippery both in extension and contraction.

7. An endoscopic device for self-propelled locomotion through a selected body cavity in a predetermined direction, comprising a hollowed, cylindrical, non-bellows type body constructed of a relatively elastic and flexible material extending between two end portions with anchors suitable for temporarily and alternately attaching the end portions to a selected wall portion of the body cavity in synch with corresponding extensions and contractions axially of the cylindrical body, and pneumatic devices for actuating the anchors, wherein walls of the cylindrical body incorporate a structure for reinforcing the cylindrical body, the structure comprising a pair of coaxial helical springs wound crosswise relative to one another, and distributed along an entire length of the cylindrical body, wherein the helical springs are rigid in a radial direction and yield in an axial direction, so as to provide elongation and contraction of the cylindrical body concurrently through such axial yieldability of the reinforcement structure while preventing radial dilation or collapse of the cylindrical body.

\* \* \* \* \*